United States Patent [19]

Howlett

[11] 4,024,865

[45] May 24, 1977

[54] SYRINGE

[75] Inventor: Donald E. Howlett, Reno, Nev.

[73] Assignee: Hamilton Company, Reno, Nev.

[22] Filed: Sept. 16, 1975

[21] Appl. No.: 613,821

[52] U.S. Cl. .......................................... 128/218 PA
[51] Int. Cl.² ............................................ A61M 5/00
[58] Field of Search ..... 128/218 R, 218 P, 218 PA, 128/216, 215, 236

[56] References Cited

UNITED STATES PATENTS

| | | | |
|---|---|---|---|
| 786,697 | 4/1905 | Wackenhuth | 128/218 P |
| 1,142,682 | 6/1915 | Dickinson | 128/218 PA |
| 1,592,335 | 7/1926 | Brody et al. | 128/218 P |
| 1,798,116 | 3/1931 | Brockway | 128/218 PA |
| 1,834,713 | 12/1931 | Kahn | 128/218 PA |
| 2,771,880 | 11/1956 | Gotthart | 128/218 P |

Primary Examiner—John D. Yasko
Attorney, Agent, or Firm—Fitch, Even, Tabin & Luedeka

[57] ABSTRACT

A syringe is described incorporating a hollow body, a plunger therein, and a needle extending axially from the hollow body. The force required to depress the plunger is controlled by a friction device engaging the plunger, the friction device being adjustable by a threaded friction screw mounted in the hollow body. A finger grip is mounted on the friction screw and may be turned to adjust the position of the friction screw relative to the body.

5 Claims, 3 Drawing Figures

SYRINGE

This invention relates generally to syringes and, more particularly, to an improved syringe employing a finger grip and in which the force required to depress the plunger of the syringe is readily adjusted.

Syringes utilized for laboratory purposes are often employed in situations where a great deal of internal pressure exists in the syringe during its operation. For example, syringes utilized in high pressure gas chromatography may operate at working pressures of over 400 atmospheres. Under such circumstances, it is convenient to employ a finger grip including a pair of transverse portions for receiving the index and middle fingers, respectively, of a person using the syringe.

Often syringes, including those of the type described, desirably employ means for adjusting the force which it takes to depress the plunger. This may include a friction device which engages the plunger with a force which is adjustable by a suitable screw means or other device. Where a finger grip is employed on a syringe, however, the incorporation of the adjustable plunger force may become unduly complex.

It is an object of the present invention to provide an improved syringe.

Another object of the invention is to provide a syringe having a finger grip and adjustable plunger force which is simple of construction and readily manufactured.

A further object of the invention is to provide an improved syringe in which the force required to depress the plunger may be readily adjusted by a simple movement of a finger grip.

Other objects of the invention will become apparent to those skilled in the art from the following description taken in connection with the accompanying drawings wherein.

Figure 1:
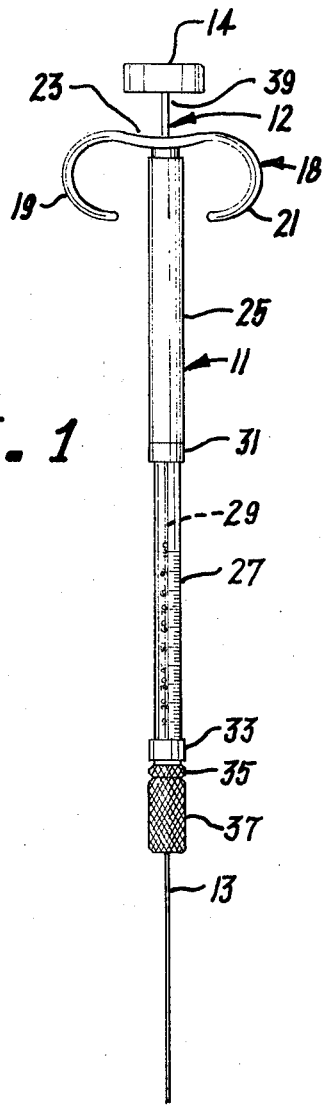
FIG. 1 is an elevational view of a syringe incorporating the invention.

Very generally, the syringe of the invention includes a hollow body 11, a plunger 12 in the hollow body, and a needle 13 extending axially from the hollow body. Means 14 are provided for manually depressing the plunger to expel the contents of the hollow body through the needle. Friction means 16 are mounted in the hollow body for frictionally engaging the plunger with a force related to the axial pressure exerted on the friction means. Friction screw means 17 threadably engage the body and are rotatable with respect thereto for movement axially thereof. The friction screw means engage the friction means for exerting axial pressure thereon dependent upon the axial position of the friction screw means with respect to the body. A finger grip 18 includes a pair of transverse portions 19 and 21 for receiving the index and middle fingers, respectively, of a person using the syringe. The finger grip has a central portion 23 joining the transverse portions and secured to the friction screw for rotating same with respect to the body.

Referring now more particularly to FIG. 1, the body of the syringe includes a tubular holder 25 and a transparent glass barrel 27 having an internal bore 29. A threaded connector 31, secured to the glass barrel 27, connects the barrel 27 with the holder 25. A threaded connector 33 is secured to the lower end of the glass barrel 27 and carries a jam nut 35 and a locking nut 37 which secure the needle 13 to the body 11.

The plunger 12 comprises a suitable assembly including an upper rod 39 axially extending from a piston, not illustrated, of reduced diameter which moves within the passage 29 in the glass barrel 27 to expel the contents of the passage 29 through the needle 13. A button 14 is mounted on the end of the rod 39 and may be depressed by the thumb of a person using the syringe to expel the contents of the glass barrel 27.

Figure 3:
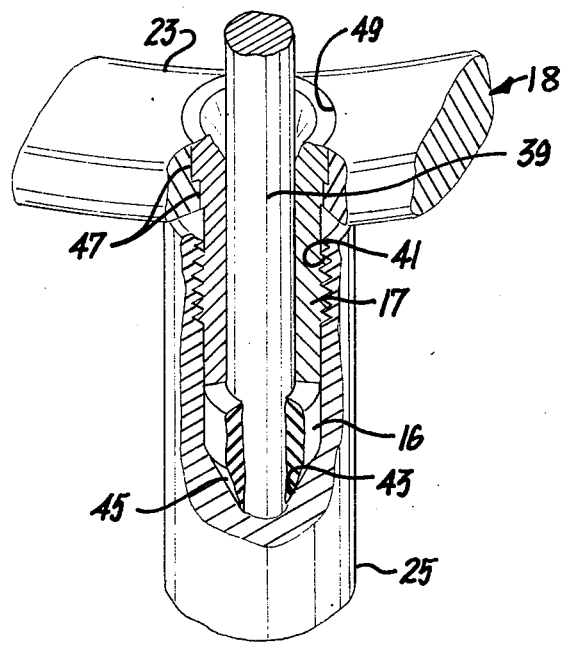
FIG. 3 is a partial view, partially broken out, of the syringe of FIG. 1, illustrating the means for adjusting the plunger force and a portion of the finger grip therein.

Referring now more particularly to FIG. 3, the upper end of the holder 25 includes internal threads 41 which engage external threads on the tubular friction screw 17. By rotating the friction screw relative to the body 25, the screw may be displaced axially with respect to the holder. As may be seen, the lower end of the friction screw 17 engages the annular member 16 at the end thereof opposite the frustoconical or inclined surface 43 internally of the holder 25. The annular member 16 constitutes the friction means and is deformed through the pressure of the friction screw 17 and the action of the inclined surface 43 to increase or decrease frictional pressure exerted against the rod 39. In this way, the force required to push the plunger may be varied to suit the particular needs required for use of the syringe.

The member 16 may be of suitable construction but in the illustrated embodiment includes an annular member having a tapered surface 45 on its lower end matching the tapered surface 43 on the interior of the holder 25. The material of which the annular member 16 is manufactured comprises any suitable deformable material which is capable of wear and of providing the necessary frictional force. A satisfactory material for this purpose is obtainable commercially under the trademark TEFLON.

The friction screw 17 is formed with stepped diameters, indicated generally at 47, near its upper end. These are received in a correspondingly shaped opening 49 formed in the central portion 23 of the finger grip 18. The screw is bonded in place in the central portion 23 of the finger grip 18 by any suitable adhesive.

Three longitudinal grooves, not shown, are provided on the internal diameter of the annular member 16 spaced symmetrically circumferentially to obtain proper balance on the rod 39 large enough in width and depth to allow air to flow along the rod past the ring and with enough surface to obtain the desired friction without collapsing.

Figure 2:
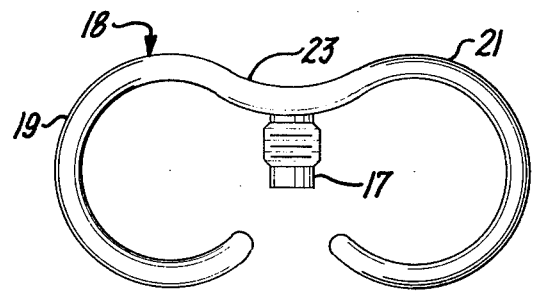
FIG. 2 is an elevational view of a finger grip and friction screw employed in the syringe of FIG. 1.

For the purpose of rotating the friction screw 17 with respect to the holder 25, the finger grip 18 is utilized. As may be seen in FIG. 2, the finger grip includes transverse portions 19 and 21 which are generally C-shaped with their open sides disposed toward each other. The central portion 23 extends between two adjacent ends of the transverse portions.

When the finger grip 18 is rotated with respect to the holder 25, the friction screw 17 may be moved toward or away from the friction device or annular member 16, thus increasing or decreasing the pressure exerted thereby against the rod 39. The amount of friction which may be developed and exerted on the rod depends upon how tightly the friction screw is forced against the annular member 16. The friction force developed is thereby infinitely variable and ranges from zero to an amount which is capable of locking the rod in place. This is readily adjusted by merely turning the finger grip, and no extra mechanical devices are required for this purpose.

It may therefore be seen that the invention provides an improved syringe in which the force required to depress the plunger is infinitely variable and is readily varied by simple movement of the finger grip employed in the syringe. The device is therefore easily manufactured and used, and is relatively simple of construction and low in cost.

Various modifications of the invention in addition to those shown and described herein will become apparent to those skilled in the art from the foregoing description and accompanying drawings. Such modifications are intended to fall within the scope of the appended claims.

What is claimed is:

1. A syringe comprising a hollow body having a barrel and an internally threaded holder, a plunger in said hollow body, a needle extending axially from said barrel of said hollow body, means for manually depressing said plunger to expel the contents of said barrel of said hollow body through said needle, friction means mounted in said holder of said hollow body, said friction means comprising an annular member of deformable material surrounding said plunger for frictionally engaging said plunger with a force related to the axial pressure exerted on said friction means, friction screw means threadably engaged with said holder of said body and rotatable with respect thereto for movement axially thereof, said friction screw means engaging said friction means for exerting axial pressure thereon dependent upon the axial position of said friction screw means with respect to said body, said holder of said body including an internal inclined surface engaging said annular member on the side thereof opposite said friction screw means, and a finger grip including a pair of transverse portions for receiving the index and middle fingers, respectively, of a person using the syringe, said finger grip having a central portion joining said transverse portions and secured to said friction screw means for rotating same with respect to said body.

2. A syringe according to claim 1 wherein said transverse portions of said finger grip are generally C-shaped with their own sides disposed toward each other, and wherein said central portion extends between two adjacent ends of said transverse portions.

3. A syringe according to claim 2 wherein said finger grip is comprised of a unitary bar pressed flat to a predetermined thickness.

4. A syringe according to claim 1 wherein said friction screw means comprise a tubular friction screw through which said plunger extends, and wherein said friction screw is secured to said central portion of said finger grip by an adhesive.

5. A syringe according to claim 4 wherein said central portion of said finger grip includes a central opening therein into which said friction screw is secured and through which said plunger passes.

* * * * *

UNITED STATES PATENT AND TRADEMARK OFFICE
CERTIFICATE OF CORRECTION

PATENT NO. : 4,024,865
DATED : May 24, 1977
INVENTOR(S) : Donald E. Howlett

It is certified that error appears in the above-identified patent and that said Letters Patent are hereby corrected as shown below:

Column 4, line 16, change "own" to ---open---.

Signed and Sealed this

Twenty-seventh Day of September 19:

[SEAL]

Attest:

RUTH C. MASON
Attesting Officer

LUTRELLE F. PARKER
Acting Commissioner of Patents and Trademarl